United States Patent [19]
Werner

[11] Patent Number: 6,114,331
[45] Date of Patent: Sep. 5, 2000

[54] SUBSTANCE SUPPRESSING ALLOGRAFT REJECTION

[76] Inventor: Ernst Werner, Hechenbergweg 10, A-6020 Innsbruck, Austria

[21] Appl. No.: 09/348,801

[22] Filed: Jul. 7, 1999

[30] Foreign Application Priority Data

Jul. 10, 1998 [EP] European Pat. Off. .............. 98112821

[51] Int. Cl.$^7$ ............................................... A61K 31/4985
[52] U.S. Cl. ............................................................ 514/249
[58] Field of Search .............................................. 514/249

[56] References Cited

FOREIGN PATENT DOCUMENTS 44 18 097 A1   11/1995   Germany .

OTHER PUBLICATIONS

S. Pfeiffer et al.: "Allosteric and Functional Effects of the Potent Pterin Antagonist of Neronal nitric Oxide Synthase 4–Amino–Tetrahydrobiopterin";Portland Press Proc., vol. 15, No. Biology of Nitric Oxide, part 6, 1998, p. 15 XP002088812, the whole document.

E.R. Werner et al.; "Identification of the 4–Amino analogue of Tetrahydrobiopterin as a Dihydropteridine Reductase Inhibitornand a Potent PteridineAntagonist of Rat Neuronal Nitric Oxide Synthase"; Biochem. J., vol. 320, No. 1, 1996, pp. 193–196, XP00208813, the whole document.

B. Meyer et al.: "Tetrahydrobiopterin binding to Macrophage Inducible Nitric Oxide synthase: Heme Spin Shift and Dimer Stabilization by the Potent Pterin Antagonist 4–Amino–Tetrahydrobiopterin"; Biochemistry, vol. 36, No. 27, 1997, pp. 8422–8427, XP002088814, abstract.

S. Pfeiffer et al.: "Allosteric Modulatipon of Rat Brain Nitric Oxide Synthase by the Pterin–Site Enzyme Inhibitor 4–Aminotetrahydrobiopterin"; Biochem. J., vol. 328, No. 2, 1997, pp. 349–352, XP002088815, abstract.

Chemical Abstracts, vol. 128, No. 26, Jun. 29, 1998, Columbus, Ohio, U.S.; avbstract No. 318679e, E.R. Werner et al.: "Binding of Pteridines to Nitric Oxide synthase by Tetrahydrobiopterin"; p. 239; XP002088816, abstract & Chem. Biol. Pteridines Folates 1997, pp. 669–673.

*Primary Examiner*—John M. Ford
*Attorney, Agent, or Firm*—Lorusso & Loud

[57] ABSTRACT

Use of a substance according to formula (I) including its tautomeric forms, stereoisomeric forms and salts

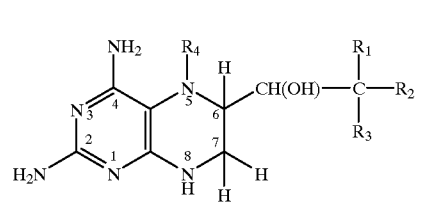

for the production of a drug suppressing the immunoreaction, in particular suppressing allograft rejection.

15 Claims, No Drawings

SUBSTANCE SUPPRESSING ALLOGRAFT REJECTION

This invention comprises pteridines with the following formula:

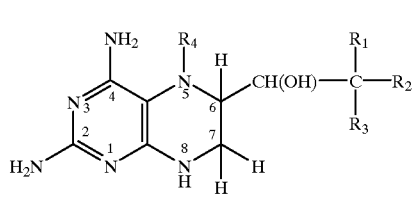

wherein $R_1$ is H or OH, $R_3$ is H or OH, $R_4$ is H, $CH_3$, $CH_2OH$ or CHO, $R_2$ is H, $CH_3$, $CH_2OH$, CHO, or lower alkyl (C1–C9), which is single chain or branched, or $(CH(OH))_n$—Y, or $(CH(OH))_n$—$(CH_2)_m$—W, wherein Y is hydrogen or lower alkyl, W is hydrogen or hydroxyl, n is 1 to 20, m is 1–20.

4-amino analoga of pteridines with the formula (I) are novel inhibitors of NO synthases (E. R. Werner et al., Biochem. J. (1996) 320, 193–196).

The invention is founded on the discovery, that the substances of formula (I) can be used to produce drugs suppressing the immunoreaction, in particular suppressing the rejection of an allograft. Theoretical considerations and experiments implicate that the various substances of formula (I) have similar physiological properties. These properties seem to result from the CH(OH)—R side chain at $C_6$ which are much more active than compounds with a $CH_2$—R side chain at $C_6$ (see DE4418097).

An example for a substance according to formula (I) is 2,4-diamino-5,6,7,8-tetrahydro-6-(L-erythro-1,2-dihydroxypropyl)-pteridine which will be called tetrahydroaminobiopterin in the following. This substance, which has been used in the experiments described below, results from formula (I) if $R_1$ and $R_4$ are hydrogen, $R_2$ is methyl, and $R_3$ is hydroxyl, and the stereochemistry is 6-(L-erythro).

Common immunosuppressive drugs to treat allograft rejection are e.g. cyclosporin A or corticosteroids. Based on the observation of increased biosynthesis of NO in allograft rejection, inhibitors of NO synthesis have been tested in animal models for their potential to reduce allograft rejection. However, reports on the effects of inhibitors of NO synthesis in animal models of allograft rejection are contradictory. Favorable action of inhibitors of NO biosynthesis for this purpose (Worall N. K. et al., Transplantation 63: 1095–1101 (1997)) as well as detrimental actions have been reported: In a murine model of graft versus host disease, inhibition of NO synthesis resulted in increased weight loss and decreased survival (Drobyski W. R. et al., Blood 84: 2363–2372 (1994)). Furthermore, survival of grafted hearts in rats was decreased by inhibition of NO synthesis (Paul L. C. et al., Transplantation 62: 1193–1195, (1996)).

Thus, the property of NO synthesis inhibition by the compounds with formula (I) does not necessarily result in its ability to inhibit allograft rejection. It is not clear whether inhibition of NO synthesis or another mechanism is responsible for the beneficial effects of the compounds of formula (I) in allograft rejection. Especially the extent of effectiveness, which is detailed in the following description of animal experiments, could not be expected.

Example of the Effect of Tetrahydroaminobiopterin in an Animal Model of Allograft Rejection To study the effect of tetrahydroaminobiopterin, an allogeneic heart transplantation model using cuff-technique was employed (described by Branched G. et al., Acta Chir. Austriaca Suppl. #130 (1997), Abstract #77). In this model, hearts from male C57B1/10 mice are grafted to male C3H/He mice and the beating of the additional heart is monitored visually from outside. Quantification of the immunosuppressive action is done by counting the days the additional heart is able to beat. Groups of five animals each (except for dose 0: three animals) were treated for seven days following transplantation with 0, 20, 100, and 200 mg/kg tetrahydroaminobiopterin (dihydrochloride; 6R:6S=60:40). Application of tetrahydroaminobiopterin was performed every 24 hours by intramuscular injection of the compound dissolved in 100 μl 0.9% (w/v) aqueous sodium chloride. Table 1 shows survival times of allografted hearts:

TABLE 1

Dependence of survival of allografted hearts in mice on the dose of tetrahydroaminobiopterin:

| dose (mg kg$^{-1}$ d$^{-1}$) | animals per group | allograft survival (days) |
|---|---|---|
| 0 | 3 | 7, 8, 7 |
| 20 | 5 | 10, 12, 10, 8, 10 |
| 100 | 5 | 11, 13, 11, 13, 13 |
| 200 | 5 | 11, 13, 14, 12, 13 |

Analysis of the data shown in Table 1 using Spearman—Rank correlation yields a highly significant increase of allograft survival with the increasing dose of tetrahydroaminobiopterin (P <0.0008).

The dosing protocol given is only an example, other dosing regimens (e.g. intravenous, oral, several applications per day, continuous infusion using a pump, depot preparations according to the state of the art) can also be used.

What is claimed is:

1. A method of suppressing an immuno reaction in humans or in animals comprising the steps of:
   dispersing in a delivery vehicle an effective amount of pteridine to suppress an immuno reaction, the pteridine having the formula

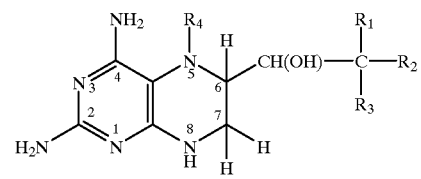

or a salt thereof, wherein $R_1$ and $R_3$ are selected from a member of the group consisting of H and OH; and
   wherein $R_4$ is selected from a member of the group consisting of H, $CH_3$, $CH_2OH$ and CHO; and
   wherein $R_2$ is selected from a member of the group consisting of H, $CH_3$, $CH_2OH$, CHO, single chain alkyl of not more than 9 carbon atoms, branched alkyl of not more than 9 carbon atoms;
   $(CH(OH))_n$—Y wherein Y is selected from a member of the group consisting of H and alkyl of not more than 9 carbon atoms; and
   $(CH(OH))_n$—$(CH_2)_m$—W wherein W is selected from a member of the group consisting of H and hydroxyl, and wherein n and m are 1 to 20;
   applying the delivery vehicle to tissue so as to bring the pteridine into contact with tissue;
   allowing the pteridine to migrate from the delivery vehicle to the tissue where the pteridine is absorbed.

2. The method according to claim 1 wherein the $R_1$ and $R_4$ of the pteridine dispersed in the delivery vehicle are hydrogen, the $R_2$ of the pteridine dispersed in the delivery vehicle is methyl, and the $R_3$ of the pteridine dispersed in the delivery vehicle is hydroxyl.

3. The method according to claim 1 wherein the pteridine that is dispersed in the delivery vehicle is 2,4-diamino-5,6,7,8-tetrahydro-6-(L-erythro-1,2-dihydroxypropyl)pteridine.

4. The method according to claim 1 wherein the pteridine that is dispersed in the delivery vehicle is selected from a member of the group consisting of tautomeric forms of the pteridine having the formula given in claim 1 and stereoisomeric forms of the pteridine having the formula given in claim 1.

5. The method of any one of the preceding claims wherein the delivery vehicle is administered a sufficient number of times such that the pteridine is allowed to suppress an immuno reaction.

6. A method for suppressing an allograft rejection in humans or in animals, the method comprising the steps of:

dispersing in a delivery vehicle an effective amount of pteridine to suppress an allograft rejection, the pteridine having the formula

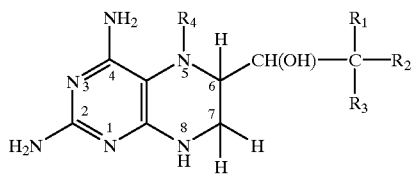

or a salt thereof, wherein $R_1$ and $R_3$ are selected from a member of the group consisting of H and OH; and wherein $R_4$ is selected from a member of the group consisting of H, $CH_3$, $CH_2OH$ and CHO; and wherein $R_2$ is selected from a member of the group consisting of H, $CH_3$, $CH_2OH$, CHO, single chain alkyl of not more than 9 carbon atoms, branched alkyl of not more than 9 carbon atoms;

$(CH(OH))_n$—Y wherein Y is selected from a member of the group consisting of H and alkyl of not more than 9 carbon atoms; and $(CH(OH))_n$—$(CH_2)_m$—W wherein W is selected from a member of the group consisting of H and hydroxyl, and wherein n and m are 1 to 20;

applying the delivery vehicle to tissue so as to bring the pteridine into contact with tissue;

allowing the pteridine to migrate from the delivery vehicle to the tissue where the pteridine is absorbed;

allowing the pteridine to supress an allograft reaction.

7. The method according to claim 6 wherein the delivery vehicle is administered by injection into tissue using a syringe containing the delivery vehicle.

8. The method according to claim 6 wherein the delivery vehicle is administered by continuous infusion into tissue using a pump.

9. The method according to claim 6 wherein the delivery vehicle is administered orally such that the delivery vehicle is swallowed.

10. The method according to claim 6 wherein the delivery vehicle is administered using a depot preparation.

11. The method according to claim 6 wherein the delivery vehicle is administered by applying the delivery vehicle to a transdermal patch, applying the transdermal patch to the skin, and allowing the pteridine to migrate from the delivery vehicle to the skin where it is absorbed by tissue.

12. The method according to claim 6 wherein the delivery vehicle selected from a member of the group consisting of creams, ointments, and liquids is directly applied to tissue such that the pteridine that is dispersed in the delivery vehicle is allowed to be absorbed from the delivery vehicle by the tissue.

13. The method according to claim 6 wherein the $R_1$ and $R_4$ of the pteridine dispersed in the delivery vehicle are hydrogen, the $R_2$ of the pteridine dispersed in the delivery vehicle is methyl, and the $R_3$ of the pteridine dispersed in the delivery vehicle is hydroxyl.

14. The method according to claim 6 wherein the pteridine that is dispersed in the delivery vehicle is 2,4-diamino-5,6,7,8-tetrahydro-6-(L-erythro-1,2-dihydroxypropyl)pteridine.

15. The method of any one of the preceding claims 6 through 14 wherein the delivery vehicle is administered a sufficient number of times such that the pteridine is allowed to suppress an allograft rejection.

* * * * *